US008680260B2

(12) United States Patent
Watanabe et al.

(10) Patent No.: US 8,680,260 B2
(45) Date of Patent: Mar. 25, 2014

(54) $^{18}$F-LABELED AZIDE COMPOUND, REAGENT FOR $^{18}$F-LABELING AND METHOD FOR $^{18}$F-LABELING OF ALKYNE COMPOUND USING SAME (75) Inventors: Yasuyoshi Watanabe, Kobe (JP); Masaaki Suzuki, Kobe (JP); Hisashi Doi, Kobe (JP); Takeshi Kuboyama, Kobe (JP); Satoshi Obika, Suita (JP); Takeshi Imanishi, Suita (JP)

(73) Assignee: Riken, Wako-Shi (JP)

( * ) Notice: Subject to any disclaimer, the term of this patent is extended or adjusted under 35 U.S.C. 154(b) by 137 days.

(21) Appl. No.: 13/320,421

(22) PCT Filed: May 14, 2010

(86) PCT No.: PCT/JP2010/058217
§ 371 (c)(1),
(2), (4) Date: Jan. 11, 2012

(87) PCT Pub. No.: WO2010/131745
PCT Pub. Date: Nov. 18, 2010

(65) Prior Publication Data
US 2012/0101266 A1 Apr. 26, 2012

(30) Foreign Application Priority Data

May 15, 2009 (JP) ................................. 2009-118505

(51) Int. Cl.
C07H 21/00 (2006.01)
(52) U.S. Cl.
USPC .......... 536/25.32; 536/23.1; 536/25.3; 552/1; 552/8
(58) Field of Classification Search
None
See application file for complete search history.

(56) References Cited

U.S. PATENT DOCUMENTS

2008/0075661 A1   3/2008   Robillard et al.

FOREIGN PATENT DOCUMENTS

| JP | 2008-515875 A | 5/2008 |
|---|---|---|
| WO | WO 2006/038184 A2 | 4/2006 |
| WO | WO 2006/116629 A2 | 11/2006 |

OTHER PUBLICATIONS

Dolle et al., "A general method for labeling oligodeoxynucleotides with 18F for in vivo PET imaging", Journal of Labelled Compounds and Radiopharmaceuticals, vol. 39, Issue 4, pp. 319-330, Apr. 1997.
Glaser et al.,""Click labeling" with 2-[18f]fluoroethylazide for positron emission tomography", Bioconjugate Chemistry, Apr. 13, 2007, vol. 18, No. 3, pp. 989-993.
Hausner et al., "In vivo positron emission tomography (PET) imaging with an avb6 specific peptide radiolabeled using 18F-"click" chemistry: evaluation and comparison with the corresponding 4-[18F]fluorobenzoyl- and 2-[18F]fluoropropionyl-peptides", Journal of Medicinal Chemistry., Sep. 12, 2008. vol. 51, Issue: 19, pp. 5901-5904.
Hedberg et al.",Synthesis of 4-([18F]Fluoromethyl)phenyl Isothiocyanate and its Use in Labeling Oligonucleotides", Acta Chemica Scandinavica, 1997, vol. 51, pp. 1236-1240.
Hedberg et al., "18F-Labelling of Oligonucleotides Using Succinimido 4-[18F]Fluorobenzoate", Acta Chemica Scandinavica, 1998, vol. 52, pp. 1034-1039.
Inkster et al., "Radiosynthesis and bioconjugation of [18F]FPy5yne, a prosthetic group for the 18F labeling of bioactive peptides", Journal of Labelled Compounds and Radiopharmaceuticals, vol. 51, Issue 14, pp. 444-452, Nov. 6, 2008.
International Search Report for PCT/JP2010/058217 dated Jun. 29, 2010.
Kim et al., "A (18)F-labeled glucose analog: synthesis using a click labeling method and in vitro evaluation", Archives of Pharmacal Research, 2008, vol. 31, Issue: 5, pp. 587-593.
Kuhnast et al., "Design and Synthesis of a New [18F]Fluoropyridine-Based Haloacetamide Reagent for the Labeling of Oligonucleotides:• 2-Bromo-N-[3-(2-[18F]fluoropyridin-3-yloxy)propyl]acetamide", Bioconjugate Chemistry, 2004, vol. 15, No. 3, pp. 617-627.
Kühnast et al., "General method to label antisense oligonucleotides with radioactive halogens for pharmacological and imaging studies", Bioconjugate Chemistry, Sep.-Oct. 2000, vol. 11, No. 5, pp. 627-636.
Lange et al., "Photoconjugation of 3-azido-5-nitrobenzyl-[18F]fluoride to an oligonucleotide aptamer", Journal of Labelled Compounds and Radiopharmaceuticals, vol. 45, Issue 3, pp. 257-268, Mar. 15, 2002.
Li et al., "Click Chemistry 18F-Labeling of RGD Peptides and microPET Imaging of Tumor Integrin • v• 3 Expression", Bioconjugate Chemistry, 2007, vol. 18, Issue: 6, pp. 1987-1994.
Marik et al., "Click for PET: rapid preparation of [18F]fluoropeptides using CuI catalyzed 1,3-dipolar cycloaddition", Tetrahedron Letters, 2006, vol. 47, Issue: 37, pp. 6681-6684.
Ramenda et al., "Synthesis of 18F-labeled Neurotensin(8-13) via Copper-Mediated 1,3-Dipolar [3+2]Cycloaddition Reaction", Letters in Drug Design & Discovery, vol. 4, No. 4, Jun. 2007 , pp. 279-285.
Sirion et al., "An efficient F-18 labeling method for PET study : Huisgen 1 , 3-dipolar cycloaddition of bioactive substances and F-18-labeled compounds", Tetrahedron Letters, 2007, vol. 48, Issue: 23, pp. 3953-3957.
Thonon et al., "New strategy for the preparation of clickable peptides and labeling with 1-(azidomethyl)-4-[(18)F]-fluorobenzene for PET", Bioconjugate Chemistry, Apr. 2009 , vol. 20, No. 4, pp. 817-823.
Vaidyanathan et al., "Labeling proteins with fluorine-18 using N-succinimidyl 4-[18F]fluorobenzoate", Nuclear Medicine Biology, International Journal of Radiation Applications and Instrumentation Part B, Apr. 1992, vol. 19, No. 3, pp. 275-281.

*Primary Examiner* — Patrick Lewis
(74) *Attorney, Agent, or Firm* — Birch, Stewart, Kolasch & Birch, LLP (57) ABSTRACT

The present invention provides an $^{18}$F-labeled azide compound usable in the Huisgen reaction which enables $^{18}$F-labeling although only a small quantity of alkyne compound is available as a counterpart substrate, more specifically the $^{18}$F-labeled azide compound enabling the PET to be applied to peptides or oligonucleotides and enabling the $^{18}$F-labeling of any sites of oligonucleotide other than the 5' end or 3' end thereof, a reagent for $^{18}$F-labeling, and a method for $^{18}$F-labeling of an alkyne compound using the same.

6 Claims, 4 Drawing Sheets fig.1 fig.2 fig.3 fig.4

```
SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: The oligonucleotide which was modified with an
      alkine group
<220> FEATURE:
<221> NAME/KEY: modified_base
<222> LOCATION: (1)..(1)

<400> SEQUENCE: 1
ccggttgctc tgagacat                                                 18

<210> SEQ ID NO 2
<211> LENGTH: 18
<212> TYPE: DNA
<213> ORGANISM: Artificial Sequence
<220> FEATURE:
<223> OTHER INFORMATION: The oligonucleotide which was labeled with 18F
<220> FEATURE:
<221> NAME/KEY: modified_base
<222> LOCATION: (1)..(1)

<400> SEQUENCE: 2
ccggttgctc tgagacat                                                 18

<210> SEQ ID NO 3
<211> LENGTH: 18
<212> TYPE: DNA
<213> ORGANISM: Artificial Sequence
<220> FEATURE:
<223> OTHER INFORMATION: The oligonucleotide which was labeled with 18F
<220> FEATURE:
<221> NAME/KEY: modified_base
<222> LOCATION: (1)..(1)

<400> SEQUENCE: 3
ccggttgctc tgagacat                                                 18
```

$^{18}$F-LABELED AZIDE COMPOUND, REAGENT FOR $^{18}$F-LABELING AND METHOD FOR $^{18}$F-LABELING OF ALKYNE COMPOUND USING SAME

FIELD OF THE INVENTION

The present invention relates to an $^{18}$F-labeled azide compound, a reagent for $^{18}$F-labeling, and a method for $^{18}$F-labeling of an alkyne compound using the same. The present invention is suitably applicable to production of a radioactive tracer indispensable for positron emission tomography (hereinafter, called "PET").

BACKGROUND OF THE INVENTION

PET is a method that includes administering, into a living body, a tracer labeled with a short-term radionuclide which releases positrons such as $^{18}$F or $^{11}$C so that γ rays generated from the tracer is measured by a PET camera (detector comprising a gamma ray scintillator and a photoelectron multiplier tube), and imaging a body distribution of the γ ray by a computer. The PET can non-invasively and quantitatively track down the movement of materials over time in vivo, therefore, is now actively employed as a very useful measurement technique in many different fields such as biology, development of pharmaceutical products, and medical services.

Examples of the short-term radionuclide used in the PET are $^{18}$F and $^{11}$C, and compounds labeled with these radionuclides are used as the tracer. There is a very broad application range for the $^{11}$C utilizing carbon atoms present in organic compounds, therefore, $^{11}$C can be considered to be an ideal radionuclide. However, the $^{11}$C has such a short half life as 20 minutes, imposing the restriction that the process from synthesis through PET measurement must be completed within a very short time frame. In contrast, the $^{18}$F having a half life longer than that of the $^{11}$C, 110 minutes, is easy to handle and widely used in, for example, $^{18}$F-labeled glucose. Despite such an advantageous half life, positrons released by the $^{18}$F decrease with time, making the PET measurement similarly difficult. Faced with such a difficulty, a fast and simplified $^{18}$F labeling method is desirably accomplished.

To prepare an $^{18}$F-labeled compound, its base material, $^{18}$F, is supplied through nuclide transformation by a cyclotron. More specifically, ions accelerated by the cyclotron are crashed into water including $^{18}$O to invite nuclide transformation from $^{18}$O to $^{18}$F. The $^{18}$F-labeled compound can be theoretically obtained when a very weak water solution including $^{18}$F ions thus obtained and a compound selected as a PET target are reacted with each other.

In fact, it is conventionally extremely difficult to directly bond $^{18}$F to the compound for the PET. Therefore, an indirect $^{18}$F labeling method is employed, wherein an intermediate compound labeled with $^{18}$F and having a functional group to be bonded to another compound (intermediate medium thus characterized is hereinafter called "$^{18}$F prosthetic group") is prepared in advance and then bonded to the compound for the PET.

Examples of properties required for the $^{18}$F prosthetic group are: 1) easily and speedily synthesizable; 2) bondable to a target compound rapidly and efficiently under temperate conditions; and 3) hardly affecting in-vivo kinetics of the target compound. To meet these requirements, an $^{18}$F prosthetic group which leverages the Huisgen reaction is currently attracting attention.

Describing the Huisgen reaction, an organic azide compound and alkynes, as a result of a [3+2] cycloaddition reaction generated therebetween, are transformed into a 1,2,3-triasole derivative (see the following chemical formula).

Chemical Formula 1

In the case where a terminal alkyne is used as the alkynes, copper (I) ions work as a catalyst, and a 1,4-disubstituted body is selectively obtained. This reaction is not disturbed by any other functional groups, if present, such as alcohol, amine, amide, ester, and halide, therefore, a target material, triaosle, can be obtained at a high yield. The reaction uneventfully advances in any of reaction solvents such as alcohol, conventional organic solvents, and water. The asides and alkynes have a number of advantages; they can be easily introduced in various organic compounds, and they do not produce excessive post-reaction waste matters. Therefore, the asides and alkynes are cited as typical examples which represent the Click Chemistry advocated by K. B. Sharpless et al. who was awarded with Nobel Prize in Chemistry.

In the studies conducted in recent years using the Huisgen reaction, azide compounds or alkyne compounds labeled with $^{18}$F are used as the $^{18}$F prosthetic group to introduce the $^{18}$F prosthetic group in any target compounds. Below are given specific examples of such studies.

Marik and Sutcliffe, University of California, Davis, fluorinated a tosylate body having an acetylene group on its molecular end in the presence of [$^{18}$F]KF and kalium scavenger (Kryptofix222) and purified through distillation so that $^{18}$F-labeled fluoroalkynes are obtained as the $^{18}$F prosthetic group (Non-Patent Document 1). Then, they generated the Huisgen reaction between the $^{18}$F prosthetic group and azidated peptide in the presence of a catalytic system including iodinated copper (I), sodium ascorbate, and di-isopropyl ethylamine as amine base to perform $^{18}$F-labeling of the peptide at room temperature for 10 minutes (see the following reaction formula).

Chemical Formula 2

They further performed $^{18}$F-labeling of $\alpha_v\beta_6$ specific peptide using the $^{18}$F prosthetic group in which n=3 in the above formula, and successfully obtained PET images in mice in vivo (Non-Patent Document 2).

Another study using the $^{18}$F prosthetic group in which n=1 in the above formula was also reported by a study group of Sungkyunkwan University, Korea (Non-Patent Document 3).

A study group representing SIEMENS MEDICAL SOLUTIONS USA, INC. reported the use of a compound comparable to n=0 in the above formula (Patent Document 1), wherein propargyl tosylate is $^{18}$F-transformed to generate an $^{18}$F prosthetic group ([$^{18}$F]-3-fluoropropyne) in a reaction container and leave the generated $^{18}$F prosthetic group unpurified, and an overly large quantity of azide substrate is added to a reaction solution to generate a coupling reaction using copper (I) acetate.

The Non-Patent Document 4 recites an example in which an $^{18}$F-labeled azide compound is used, wherein the Huisgen reaction is generated with oligopeptide having a terminal acetylene group by using [$^{18}$F] fluoroethylene azide as $^{18}$F so that the oligopeptide is successfully labeled with $^{18}$F (see the following chemical formula).

A study group of Stanford University purified the $^{18}$F prosthetic group by employing preparative HPLC more easily automatable than distillation to thereby obtain an $^{18}$F-labeled alkyne compound having a high purity (Non-Patent Document 6). They generated the Huisgen reaction using a catalytic system including copper sulfate—sodium ascorbate but no amine base to label ligands of integrin $\alpha_v\beta_3$ with $^{18}$F and captured PET images in mice.

A study group of Dresden-Rossendor Research Center, Germany purified 4-[$^{18}$F]Fluoro-N-(prop-2-ynyl)benzamide synthesized by the following method by employing SPE (solid phase extraction) and used the purified material as the $^{18}$F prosthetic group, and then performed the $^{18}$F-labeling of Chemical Formula 3

A study group of Inha University, Korea reported the use of a plurality of $^{18}$F-labeled alkyne compounds and $^{18}$F-labeled azide compounds (see the following chemical formula) as the $^{18}$F prosthetic group, wherein they performed $^{18}$F-labeling of a variety of substrates (see the Non-Patent Document 5). However, their method directly performing the coupling reaction without purifying the $^{18}$F prosthetic group similarly uses an overly large quantity of compounds to be $^{18}$F-labeled as the $^{18}$F prosthetic group.

Chemical Formula 4 azidated Neurotensin (8-13) peptide through the Huisgen reaction (Non-Patent Document 7).

Chemical Formula 5

They discussed the conditions of the Huisgen reaction to reduce the quantity of peptide used in each $^{18}$F-labeling test, and found out that an optimal condition is to use the catalytic system including copper sulfate and sodium ascorbate with a borate buffer, and finally succeeded in reducing the quantity of azidated Neurotensin (8-13) peptide to 1 mg (approximately 1 μmol). However, it is necessary to further reduce the quantity for practical use.

A study group of TRIUMF, Canada, based on their hypothesis that aryl fluorine is probably more metabolically stable than aliphatic fluorine, developed an aryl fluorine $^{18}$F prosthetic group synthesizable in one stage, which was reported in 2008 (Non-Patent Document 8).

More specifically describing their study, a position 2 nitro group or trimethyl ammonio group of the pyridine derivative expressed by the following chemical formula is fluorinated and purified by the HPLC so that an $^{18}$F prosthetic group having a high purity is obtained, and the $^{18}$F prosthetic group was subjected to the Huisgen reaction with a compound to be $^{18}$F-labeled (azidated peptide precursor) in the presence of a catalytic system including TBTA, Cu (CH$_3$CN)$_4$PF$_6$ and diisopropyl ethylamine. The quantity of the compound to be $^{18}$F-labeled used in their study was, however, 1,400 nmol. This is still a large quantity which needs to be reduced.

Chemical Formula 6

X = NO$_2$ or
X = [NMe$_3$][SO$_3$CF$_3$]

In recent years, the gene therapy based on such phenomena as antisense, antigene, decoy, and RNA interference is increasingly progressing. There are ongoing approaches for the gene therapy using natural nucleic acids (DNA, RNA) or artificial nucleic acids having better pharmacological kinetics and physiological activities than natural nucleic acids (DNA, RNA) (for example, 2'-0-MeRNA, phosphorothioate oligo, BNAs, LNA). When it succeeds to label the oligonucleotide of any natural or artificial nucleic acid with $^{18}$F and administer the $^{18}$F-labeled oligonucleotide to a human or an experimental animal as a PET probe to measure intra-body kinetics using a PET camera, studies and researches of oligonucleotides are expected to further advance, accelerating the development of pharmaceutical products in which the technique is leveraged. Further, once the "double strand with complementary strand", which is a characteristic phenomenon of oligonucleotides, can be observed in vivo by using the $^{18}$F-labeled oligonucleotide (in vivo hybridization), it is facilitated to measure an in-vivo mRNA expression level. This technique is broadly applicable to diagnostics of diseases, and studies and researches of medicine and pharmacy. To meet the needs described so far, the oligonucleotide $^{18}$F-labeling method was so far often studied and reported (for example, Non-Patent Documents 9 to 14).

PRIOR ART DOCUMENTS

Patent Document

Patent Document 1: WO2006/116629

Non-Patent Documents

Non-Patent Document 1: Marik, J.; Sutcliffe, J. L. Tetrahedron Lett. 2006, 47, 6681-6684.
Non-Patent Document 2: Hausner, S. H.; Marik, J.; Gagnon, M. K. J.; Sutcliffe, J. L. J. Med. Chem. 2008, 51, 5901-5904.
Non-Patent Document 3: Kim, D. H.; Choe, Y. S.; Jung, K. -H.; Lee, K. -H.; Choi, J. Y.; Choi, Y.; Kim, B. -T. Arch. Pharm. Res. 2008, 31, 587-593.
Non-Patent Document 4: Glaser, M.; Arstad, E. Bioconjugate Chem. 2007, 18, 989-993.
Non-Patent Document 5: Sirion, U.; Kim, H. J.; Lee, J. H.; Seo, J. W.; Lee, B. S.; Lee, S. J.; Oh, S. J.; Chi, D. Y. Tetrahedron Lett. 2007, 48, 3953-3957.
Non-Patent Document 6: Li, Z. B.; Wu, Z.; Chen, K.; Chin, F. T.; Chen, X. Bioconjugate Chem. 2007, 18, 1987-1994.
Non-Patent Document 7 Ramenda, T.; Bergmann, R.; Wuest, F. Lett. Drug Des. Discovery 2007, 4, 279-285.
Non-Patent Document 8 Inkster, J. A. H.; Guerin, B.; Ruth. T. J.; Adam, M. J. J. Labelled Compd. Radiopharm. 2008, 51, 444-452.
Non-Patent Document 9: Dolle, F.; Hinnen, F.; Vaufrey, F.; Tavitian, B.; Crouzel, C. J. Labelled Compd. Radiopharm. 1997, 39, 319-330.
Non-Patent Document 10: Kuhnast, B.; Dolle, F.; Terrazzino, T.; Rousseau, B.; Loc'h, C.; Vaufrey, F.; Hinnen, F.; Doignon, I.; Pillon, F.; David, C.; Crouzel, C.; Tavitian, B. Bioconjugate Chem. 2000, 11, 627-636.
Non-Patent Document 11: Kuhnast, B.; de Bruin, B.; Hinnen, F.; Tavitian, B.; Dolle, F. Bioconjugate Chem. 2004, 15, 617-627.
Non-Patent Document 12: Hedberg, E.; Langstrom, B. Acta Chem. Scand. 1997, 51, 1236-1240.
Non-Patent Document 13: Hedberg, E.; Langstrom, B. Acta Chem. Scand. 1998, 52, 1034-1039.
Non-Patent Document 14: Christopher, W. L.; VanBrocklin, H. F.; Taylor, S. E. J. Label. Compd. Radiopharm. 2002, 45, 257-268.

SUMMARY OF THE INVENTION

Problem to be Solved by the Invention

As described so far, variously different $^{18}$F-labeled azide compounds and $^{18}$F-labeled alkyne compounds were synthesized to be used as the $^{18}$F prosthetic group to perform the $^{18}$F-labeling through the Huisgen reaction. Further, kinetics of the $^{18}$F-labeled compounds were studied by the PET. However, it was always necessary to use a large quantity of acetylene group-modified substrates as a counterpart of the reaction in the case of the $^{18}$F-labeled azide compounds, and it was always necessary to use a large quantity of azide group-modified substrates as a counterpart of the reaction in the case of the $^{18}$F-labeled alkyne compounds probably because of a reason described below.

The Huisgen reaction per se is received in the field of organic chemistry as an easy-to-handle reaction that can rapidly and easily advance when an azide compound and alkyne are simply mixed with each other in the presence of a copper (I) catalyst. However, the Huisgen reaction used in combination with the $^{18}$F-labeling, which is totally different to the Huisgen reaction alone, is very difficult to perform because a cyclotron can only produce a very small quantity of $^{18}$F, leaving no choice but to use a very low-concentrated $^{18}$F prosthetic group. According to the reaction kinetics, a reaction rate is calculated from the function of a reaction rate constant and a reaction substrate. When the low-concentrated $^{18}$F prosthetic group is used for the Huisgen reaction, therefore, it is necessary to choose any reaction system having a large reaction rate constant or increase the concentration of any compound as a labeling target. However, none of the conventional reaction systems was designed to have a substantially large reaction rate constant. Under the circumstances, there was no option but to increase the concentration of any compound to be labeled. Therefore, the quantity of any compound to be labeled was inevitably increased. In the case where the compound to be labeled is such a material that requires considerable time and cost when isolated from natural products or variously synthesized in a large quantity such as oligopeptides or oligonucleotides, only a limited number of PET images may be captured, however, any full-scale PET studies using a number of sequences of oligopeptides or oligonucleotides are still difficult. So far, there is no known example in which oligonucleotides were $^{18}$F-labeled through the Huisgen reaction.

The Non-Patent Documents 9 to 14 report the oligonucleotide $^{18}$F-labeling studies without using the Huisgen reaction. Employing any of the methods reported in these documents for performing the PET, it is still necessary to prepare a large quantity of oligonucleotide precursors that requires considerable time and cost for obtaining a large quantity and a wide variety. Therefore, the reported methods were not applicable to practical use. Further, these methods can only perform the $^{18}$F-labeling of the 5' end or 3' end of oligonucleotide, while failing to perform the $^{18}$F-labeling of any other sites thereof. These facts resulted in a small quantity of oligonucleotide precursors that can be used, leading to a strong demand for an $^{18}$F-labeling method that allows a large number of options for parts to be labeled.

The present invention was accomplished to solve the conventional problems. The present invention provides an $^{18}$F-labeled azide compound usable in the Huisgen reaction which enables $^{18}$F-labeling although only a small quantity of alkyne compound is available as a counterpart substrate, more specifically the $^{18}$F-labeled azide compound enabling the PET to be applied to peptides or oligonucleotides and enabling the $^{18}$F-labeling of any sites of oligonucleotide other than the 5' end or 3' end thereof, a reagent for $^{18}$F-labeling, and a method for $^{18}$F-labeling of an alkyne compound using the same.

Means for Solving the Problem

To solve the conventional problems, the inventors of the present invention discussed preferable designs of an $^{18}$F-labeled azide compound when applied to the PET. Prior to the $^{18}$F-labeling, a compound having a small molecular weight is preferably selected to minimize any impact on in vivo kinetics of a compound subjected to the PET. An ideal example of the compound in this regard could be $^{18}$FCH$_2$N$_3$. However, this material having a low boiling point is easily gasified, therefore, practically unusable to avoid the risk of radiation exposure. Therefore, the compound to be selected preferably has a relatively high boiling point. The compound to be selected is desirably capable of absorbing strong UV that can be detected by a UV detector of a high-performance liquid chromatography (hereinafter, called "HPLC") apparatus to facilitate post-synthesis purification and concentration, and designed to have such a boiling point that melted fractions will not be volatilized when concentrated. Further, the compound is desirably synthesizable in one stage from a precursor of the $^{18}$F-labeled azide compound and chemically stable.

A candidate of the compound meeting the required properties adduced by the inventors of the present invention is a phenyl azide compound labeled with $^{18}$F. Because of a difficulty in converting hydrogen of a phenyl group into fluorine, the inventors discussed introduction of a fluoroalkyl group in the phenyl group and tried to figure out a design that allows a smallest fluoromethyl group to be introduced. The inventors synthesized a compound which conforms to the design, and performed the Huisgen reaction between the compound and acetylene group-modified oligonucleotide. Then, they found out that their approach solves the conventional problems, and finally completed the present invention.

An $^{18}$F-labeled azide compound according to the present invention is expressed by the following structural formula 1).

Chemical Formula 7

(1)

The $^{18}$F-labeled azide compound has an azide group and thereby generates the Huisgen reaction with a compound having a carbon-carbon triple bond. Because of the structural characteristic, the $^{18}$F-labeled azide compound can be used as a reagent for $^{18}$F-labeling.

According to the finding by the inventors of the present invention, the $^{18}$F-labeled azide compound can be transformed speedily and easily into an $^{18}$F-labeled triasole derivative by the Huisgen reaction with an alkyne compound in the presence of a copper compound catalyst. As compared to the Huisgen reaction using the conventional $^{18}$F-labeled azide compound, this reaction advances although the alkyne compound, which is a counterpart substrate, is low-concentrated. Therefore, this reaction is applicable to the $^{18}$F-labeling of peptides and oligonucleotides characterized in difficulty of preparing a large quantity of substrates.

The reaction is preferably performed in the presence of ascorbate and an amine-based base by using a mixed solvent including water and a water-soluble organic solvent as s reaction solvent. Examples of the water-soluble organic solvent are; diphenyl sulfone, dimethyl sulfoxide, benzophenone, tetrahydrothiophene-1,1-dioxide, N,N-dimethylacetamide, N-methyl-2-pyrrolidinone, N-methyl-ε-caprolactam, 1,3-dimethyl-2-imidazolidinone, methanol, ethanol, n-propanol, i-propanol, n-butanol, i-butanol and t-butanol. Of these examples, dimethylsulfoxide (hereinafter, called DMSO) is particularly a suitable example because of its remarkable resolving power, good safety, less corrosiveness, good handleability because of its moderate melting point and boiling point, and good yield. Examples of the amine-based base are; diisopropyl ethylamine, triethylamine, pyridine, 2,6-lutidine, and (tris((1-benzyl-1H-1,2,3-triasole-4-yl)methyl) amine. Of these examples, (tris((1-benzyl-1H-1,2,3-triasole-4-yl)methyl)amine (hereinafter, called "TBTA") is a particularly preferable example.

The alkyne compound used in an alkyne compound $^{18}$F-labeling method according to the present invention can be a nucleotide derivative. An oligonucleotide is a biological molecule applicable to pharmaceutical products because of its physiological activity based on such phenomena as antisense, antigene, decoy, and RNA interference. Further, there are ongoing studies of artificial nucleic acids having better pharmacological kinetics and physiological activities than natural nucleic acids (DNA, RNA) (for example, 2'-0-MeRNA, phosphorothioate oligo, BNAs, LNA). When it succeeds to label the oligonucleotide of any natural or artificial nucleic acid with $^{18}$F and administer the $^{18}$F-labeled oligonucleotide to a human or an experimental animal as a PET probe to measure intra-body kinetics using a PET camera, studies and researches of oligonucleotides are expected to further advance, accelerating the development of pharmaceutical products in which the technique is leveraged.

The alkynyl group-modified oligonucleotide enables the $^{18}$F-labeling of not only the 5' end or 3' end of oligonucleotide but also any other sites thereof. Thus, any sites of oligonucleotide other than the 5' end or 3' end thereof can be successfully $^{18}$F-labeled.

DESCRIPTION OF EMBODIMENTS

Hereinafter, examples of the present invention are described in detail.

Synthesis of 4-methyl benzenesulfonic acid 4-azide benzyl (3a)

First, 4-methyl benzenesulfonic acid 4-azide benzyl (3a), which is used as a precursor of the $^{18}$F-labeled azide compound according to the present invention, was synthesized by the method expressed by the following reaction formula.

Chemical Formula 8

4-azidebenzyl alcohol (2a) (prepared by the method recited in (Andersena, J. et al.; Synlett 2005, 14, 2209-2213) (149 mg, 1.00 mmol) was dissolved in methylene chloride (5.0 mL), and pyridine (0.162 mL, 2.00 mmol) and p-toluenesulfonic acid (343 mg, 1.05 mmol) were added thereto at 0° C. After the mixed matter was agitated for 30 minutes, water is added thereto, and the resulting solution was quenched. An aqueous layer of the solution was removed therefrom, and an organic layer thereof was washed sequentially with 1 mol/L hydrochloric acid, saturated sodium acid carbonate water solution, and saturated salt solution and then dried with anhydrous sodium sulfate. Then, the solvent was distilled away under a reduced pressure. A residue thereby obtained was mixed with diethyl ether (3 mL) and then filtered through a plug of cotton to remove any insoluble matters therefrom. The filtered solution was mixed with hexane (5 mL) and agitated, and then left at rest for 30 minutes so that crystals were deposited. A supernatant liquid thereby obtained was removed from the solution by means of a pipette. The crystals were washed with hexane and then dried under a reduced pressure so that 4-methyl benzenesulfonic acid 4-azide benzyl (3a) (218 mg, 0.719 mmol, 71.9%) was obtained in the form of colorless crystals. Below are recited $^1$H-NMR spectrum, $^{13}$C-NMR spectrum, and mass spectrum (EI) of the obtained material.

$^1$H-NMR (400 MHz, CDCl$_3$)

δ: 2.45 (3H, s), 5.02 (2H, s), 6.97 (2H, d, J=8.3 Hz), 7.24 (3H, d, J=8.3 Hz), 7.34 (2H, d, J=8.3 Hz), 7.79 (2H, d, J=8.3 Hz)

$^{13}$C-NMR (100 MHz, CDCl$_3$)

δ: 21.7, 71.3, 119.2, 127.9, 129.9, 129.9, 130.3, 133.3, 141.0, 144.9

HRMS (EI)

calc 303.0677 obs 303.0650

Synthesis of 4-methyl benzenesulfonic acid 3-azide benzyl (3b)

In a manner similar to the description given earlier, 4-methyl benzenesulfonic acid 3-azide benzyl (3b), which is an isomer of the compound (3a), was obtained by the yield of 51.8%.

Chemical Formula 9

Below are recited IR spectrum, $^1$H-NMR spectrum, $^{13}$C-NMR spectrum, mass spectrum (EI), and element analysis of the obtained material.

IR (film, KBr)

2114, 1593, 1489, 1452, 1360, 1292, 1177, 945, 835, 814, 781, 665 cm$^{-1}$

$^1$H-NMR (400 MHz, CDCl$_3$)

δ: 2.45 (3H, s), 5.03 (2H, s), 6.85 (1H, s), 6.97 (1H, d, J=7.8 Hz), 7.03 (1H, d, J=7.8 Hz), 7.30 (1H, t, J=7.8 Hz), 7.33 (2H, d, J=8.5 Hz), 7.79 (2H, d, J=8.5 Hz)

$^{13}$C-NMR (100 MHz, CDCl$_3$)

δ: 21.6, 71.0, 118.8, 119.5, 124.7, 128.0, 129.9, 130.1, 133.1, 135.3, 140.5, 145.0

LRMS (EI)

calc 303 obs 303

Element Analysis calc. H, 4.32%; C, 55.43%; N, 13.85%.

obs. H, 4.32%; C, 55.59%; N, 13.89%.

Synthesis of Acetylene Group-Modified Oligonucleotide

Synthesis of Acetylene Group-Modified Oligonucleotide (4a)

Next, an acetylene group-modified oligonucleotide (4a) (sequence in the formula presents natural DNA) was synthesized by the method recited in the following literature (S. Obika, et al. Bioorganic and Medicinal Chemistry Letters, 2009, 19, 3316-3319) as an alkyne compound used as the substrate of the Huisgen reaction.

Chemical Formula 10

(4a)

O-CCGGTTGCT-
CTGAGACAT-3'

Synthesis of Acetylene Group-Modified Oligonucleotide (4b)

Then, an acetylene group-modified oligonucleotide precursor (4b) (underscored part in the following chemical formula represents 2',4'-BNA, and other parts represent natural DNA, "s" in the formula represent a phosphorothioate bond) having 2',4'-BNA (also called LNA, see the following chemical formula) and a phosphorothioate bond was synthesized as an artificial nucleic acid by the method recited in the following literature (S. Obika, et al. Bioorganic and Medicinal Chemistry Letters, 2009, 19, 3316-3319).

Chemical Formula 11

Chemical Formula 12

(4b)

O-sCsCsGsGsTsTsGsCsTs
CsTsGsAsGsAsCsAsT-3'

Synthesis of Acetylene Group-Modified Oligonucleotide (4b)

Further, an acetylene group-modified oligonucleotide precursor (4c) (underscored part in the following chemical formula represents 2',4'-BNA, and other parts represent natural DNA) in which 2' and 4' positions of deoxyribose are crosslinked was synthesized by the method recited in the following literature (S. Obika, et al. Bioorganic and Medicinal Chemistry Letters, in press, oi:10.1016/j.bmcl.2009.04.063).

Chemical Formula 13

(4c)

O-CCGGTTGCT-
CTGAGACAT-3'

Synthesis of $^{18}$F-Labeled Azide Compound and $^{18}$F-Labeling of Acetylene Group-Modified Oligonucleotide Then, the $^{18}$F-labeled azide compound was synthesized by means of the 4-methyl benzenesulfonic acid-4-azide benzyl (3a) and 4-methyl benzenesulfonic acid-3-azide benzyl (3b) synthesized earlier. Further, a coupling reaction was performed between the $^{18}$F-labeled azide compound and the acetylene group-modified oligonucleotide through the Huisgen reaction.

Example 1

In an example 1, a tosylate group of the 4-methyl benzenesulfonic acid 4-azide benzyl (3a) was substituted with $^{18}$F to synthesize an $^{18}$F-labeled azide compound (1a). Then, the coupling reaction was performed between the compound and the acetylene group-modified oligonucleotide (4a) through the Huisgen reaction. Hereinafter, the example 1 is described in detail.

Chemical Formula 14

(3a)

(1a)

(5a)

Synthesis of $^{18}$F-Labeled Azide Compound (1a)

The [$^{18}$O] water (approximately 2 mL, supplied by TAIYO NIPPON SANSO CORPORATION) was irradiated by a 12-meV electronic beam (HM-12S supplied by Sumitomo Heavy Industries, Ltd., current value: 50 μA, for 30 minutes)

so that [$^{18}$F] fluorine ions were generated. An approximately 50-GBq fluoroion [$^{18}$O] water solution thus obtained was guided in a labeling synthesis apparatus (GNMS-α, supplied by GNMS-ALPHA DAINIPPON SEIKI CO., LTD.) installed in a hot cell, and let through an anion-exchange resin cartridge (SAIKA-SPE SAX-30, supplied by AiSTI SCIENCE). The [$^{18}$F] fluorine ions adsorbed thereto were removed by carbonic acid hydrogenion tetra N-butyl ammonium (0.025 mol/L, 80% acetonitrile/water solution, 0.6 mL), and washed with 0.6 mL of acetonitrile. Then, the [$^{18}$F] fluoroion solution was guided in a first reaction container and heated to 110° C. to be dried and solidified under a reduced pressure in helium flow, and further azeotropically dried with acetonitrile (1 mL). A residual thereby obtained is mixed with an acetonitrile (1 mL) solution of 4-methyl benzenesulfonic acid 4-azide benzyl (1a) (6.0 mg) and subjected to a reaction at 85° C. for five minutes. A radiochemical yield obtained by analysis at the time was 99%. The reaction mixture was isolated and purified by semi-preparative HPLC (conditions: COSMOSIL MS-11, 10×250 mm column supplied by NAKALAI TESQUE INC., dipped in 40% acetonitrile/water for six minutes and then dipped in 60% acetonitrile/water for 14 minutes, flow rate: 1 mL/min., target material was eluted after retained for 15 to 16 minutes).

$^{18}$F-Labeling of Acetylene Group-Modified Oligonucleotide (4a) Using $^{18}$F-Labeled Azide Compound (1a)

All the fractions including the $^{18}$F-labeled azide compound (1a) thus isolated and purified were gathered and transferred to a second reaction container already containing therein 0.18 mL of DMSO. Under a reduced pressure in helium flow while being heated to 40° C., acetonitrile was carefully volatilized. To the DMSO water-mixed solution (about 0.5 mL) of the $^{18}$F-labeled azide compound (1a) thus obtained was added a buffer (100 mmol/L sodium biphosphate buffer, pH: 7.0, 60 μL), acetylene group-modified oligonucleotide (4a) (0.50 mmol/L water solution, 40 μL), copper sulfate (50 mmol/L water solution, 12 μL), TBTA (tris(1-benzyl-1H-1,2,3-triasole-4-yl)methyl)amine, 50 mmol/L DMSO solution (6 μL), and sodium ascorbate (50 mmol/L water solution, 12 μL) to generate a reaction at 40° C. for 15 minutes. A radiochemical yield obtained by analysis at the time was 92%. The reaction mixture was diluted with water (0.3 mL), and then isolated and purified by semi-preparative HPLC (conditions: COSMOSIL AR-11, 10×250 mm column supplied by NAKALAI TESQUE INC., column temperature: 50° C., linearly gradient in a 10-20% CH3CN/0.1 mol/L TEAA buffer for 20 minutes, flow rate: 4 mL/min., target material was eluted after retained for 14 to 15 minutes). All the fractions including targeted [$^{18}$F] (5a) were gathered, and acetonitrile was evaporated under a reduced pressure, so that a TEAA buffer solution (5 mL) of $^{18}$F-labeled oligonucleotide (5a) was obtained.

Time for and Yield of Synthesis of $^{18}$F-Labeled Oligonucleotide (5a)

A length of time required for synthesizing the $^{18}$F-labeled oligonucleotide (5a) and a yield thereof was; synthesis time: 84 minutes, radiation of isolated (5a): 2.53 GBq, specific radioactivity: 2366 GBq/μmol, chemical purity (UV 260 nm): 95%, radiation chemical purity: 87%, radiochemical yield based on [$^{18}$F] fluorine ions: 5.2% (not decay-compensation), and 8.6% (decay-compensated).

The synthesizing method can desalinate or concentrate TEAA if necessary. Below are described in detail desalination steps.

The TEAA buffer solution of [$^{18}$F] (5a) was let through Sep-Pak Plus C18 (supplied by Nihon Waters K.K., preconditioned with 40 mL of EtOH and 40 mL of water) and washed with water (5 mL) twice, and then dried for one minute in nitrogen gas flow so that [$^{18}$F] (5a) was eluted with ethanol (1 mL). Then, the ethanol was volatilized in nitrogen gas flow to obtain a concentrated [$^{18}$F] (5a) water solution. This water solution was diluted with a suitable volume of physiological salt solution so that a solution to be administered to animals was prepared. Although the process time further increased by 30 minutes, 90% was recovered (decay-compensated).

Example 2

Similarly to the synthesis in the example 1, a tosylate group of the 4-methyl benzenesulfonic acid-3-azide benzyl (3b) was substituted with $^{18}$F to synthesize an $^{18}$F-labeled azide compound (1b). Then, the coupling reaction was performed between the compound and the acetylene group-modified oligonucleotide (4a) through the Huisgen reaction.

Although not described in the examples because it is explicitly known from the technical common knowledge, an $^{18}$F-labeled ortho-azide compound can be obtained through an operation performed similarly to the example 1 by using 2-azidebenzyl alcohol in place of 4-azidebenzyl alcohol (2a) used as a parent material in the example 1.

Chemical Formula 15

Synthesis of $^{18}$F-Labeled Azide Compound (1b)

Similarly to the synthesis of the $^{18}$F-labeled azide compound (1a) in the example 1, the $^{18}$F-labeled azide compound (1b) was synthesized.

Labeling of Acetylene Group-Modified Oligonucleotide (4a) Using $^{18}$F-Labeled Azide Compound (1b)

Similarly to the method described in the example 1, the acetylene group-modified oligonucleotide (4a) was labeled by using the $^{18}$F-labeled azide compound (1b). The coupling reaction was performed between the $^{18}$F-labeled azide compound (1b) and the acetylene group-modified oligonucleotide (4a) through the Huisgen reaction, so that a TEAA buffer solution (5 mL) of $^{18}$F-labeled oligonucleotide (5b) was obtained.

Time for and Yield of Synthesis of $^{18}$F-Labeled Oligonucleotide (5b)

A length of time required for synthesizing the $^{18}$F-labeled oligonucleotide (5b) and a yield thereof were; synthesis time: 83 minutes, radiation of isolated (5b): 2.12 GBq, specific radioactivity: 1809 GBq/µmol, chemical purity (UV 260 nm): 99%, radiation chemical purity: 93%, radiochemical yield based on [$^{18}$F] fluorine ions: 4.2% (not decay-compensation), and 7.2% (decay-compensated).

Example 3

In an example 3, similarly to the synthesis in the example 2, a tosylate group of the 4-methyl benzenesulfonic acid-3-azide benzyl (3b) was substituted with $^{18}$F to synthesize the $^{18}$F-labeled azide compound (1b). Then, the coupling reaction was performed between the compound and the acetylene group-modified oligonucleotide (4b) through the Huisgen reaction.

Chemical Formula 16

$^{18}$F-Labeling of Acetylene Group-Modified Oligonucleotide (4b)

The coupling reaction was performed between the $^{18}$F-labeled azide compound (1b) thus synthesized and the acetylene group-modified oligonucleotide (4b) through the Huisgen reaction similarly to the method in the example 2, so that an $^{18}$F-labeled oligonucleotide (5c) was obtained.

Time for and Yield of Synthesis of $^{18}$F-Labeled Oligonucleotide (5c)

A length of time required for synthesizing the $^{18}$F-labeled oligonucleotide (5c) and a yield thereof were; synthesis time: 95 minutes, radiation of isolated (5c): 0.862 GBq, specific radioactivity: 762 GBq/µmol, chemical purity (UV 260 nm): 96%, radiation chemical purity: >99%, radiochemical yield based on [$^{18}$F] fluorine ions: 1.7% (not decay-compensation), and 3.1% (decay-compensated).

Example 4

In an example 4, similarly to the synthesis in the example 2, a tosylate group of the 4-methyl benzenesulfonic acid-3-azide benzyl (3b) was substituted with $^{18}$F to synthesize the $^{18}$F-labeled azide compound (1b). Then, the coupling reaction was performed between the compound and the acetylene group-modified oligonucleotide (4c) through the Huisgen reaction.

Chemical Formula 17

$^{18}$F-Labeling of Acetylene Group-Modified Oligonucleotide (4c)

The coupling reaction was performed between the $^{18}$F-labeled azide compound (1b) thus synthesized and the acetylene group-modified oligonucleotide (4b) through the Huisgen reaction, so that an $^{18}$F-labeled oligonucleotide (5d) was obtained.

Time for and Yield of Synthesis of $^{18}$F-Labeled Oligonucleotide (5d)

A length of time required for synthesizing the $^{18}$F-labeled oligonucleotide (5d) and a yield thereof were; synthesis time: 83 minutes, radiation of isolated (5c): 1.66 GBq, specific radioactivity: 3205 GBq/µmol, chemical purity (UV 260 nm): 98%, radiation chemical purity: 96%, radiochemical yield based on [$^{18}$F] fluorine ions: 3.3% (not decay-compensation), and 5.6% (decay-compensated).

Comparison to the Prior Art

It was confirmed form the results of the examples 1 to 3 that the alkyne compound can be $^{18}$F-labeled at a high yield when the Huisgen reaction is performed between the $^{18}$F-labeled azide compounds (1a) and (1b) which are very dilute and the acetylene group-modified oligonucleotides which are very dilute in the presence of the copper compound catalyst. Table 1 shows required quantities and concentrations of compounds to be $^{18}$F-labeled in the conventional $^{18}$F-labeling method and the $^{18}$F-labeling method according to the present invention. As compared to the conventional $^{18}$F-labeling method, the $^{18}$F-labeling using the $^{18}$F-labeled azide compounds (1a) and (1b) according to the examples 1 to 3 can be accomplished although the required quantities and concentrations of the compounds to be $^{18}$F-labeled are significantly small as is clearly known from the table.

Chemical Formula 18

4 mM

TABLE 1

|  |  | quantity of compound to be $^{18}$F-labeled (nmol) | concentration of compound to be $^{18}$F-labeled (μmol/L) |
| --- | --- | --- | --- |
| oligonucleotide | method recited in the Non-patent Document 9 | 100-200 |  |
|  | method recited in the Non-patent Document 10 | 200-400 | 200-400 |
|  | method recited in the Non-patent Document 11 | 141-275 | 353-688 |
|  | method recited in the Non-patent Document 12 | 70 | 778 |
|  | method recited in the Non-patent Document 13 | 52-140 | 520-1040 |
|  | method recited in the Non-patent Document 14 | 76-600 | 688-5503 |
| Huisgen reaction | method recited in the Non-patent Document 1 | 300 | 136 |
|  | method recited in the Non-patent Document 2 | 400 | 533 |
|  | method recited in the Non-patent Document 3 | 48700 | 37462 |
|  | method recited in the Non-patent Document 4 | 3400 | 17000 |
|  | method recited in the Non-patent Document 5 | 15000 | 30000 |
|  | method recited in the Non-patent Document 6 | 678 | 565 |
|  | method recited in the Non-patent Document 7 | 1000 | 12500 |
|  | method recited in the Non-patent Document 8 | 1400 | 9333 |
|  | $^{18}$F-labeled azide compounds (1a) and (1b) | 10-20 | 10-40 |

The Non-Patent Documents 1 to 8 recite the $^{18}$F-labeling methods using the Huisgen reaction, whereas the Non-Patent Documents 9 to 14 recite the conventional methods wherein oligonucleotide is $^{18}$F-labeled.

Reaction Conditions

To perform the $^{18}$F-labeling through the Huisgen reaction using the $^{18}$F-labeled azide compound according to the present invention, the synthesis is preferably performed remotely by using a mechanical device to avoid exposure to radiation. To serve the purpose, it is desirable to use a labeling synthesis apparatus in a shielded draft. As a result, it becomes necessary to meet within a limited amount of time such a need to obtain a trace level of 18F-labeled azide compound having a very high purity from large quantities of precursors, resolved matters, and different reagents. Moreover, the Huisgen reaction per se should speed up and achieve a high yield. To meet all of these needs, optimal reaction conditions were thoroughly discussed.

Optimal Conditions for Huisgen Reaction

To efficiently perfrom the Huisgen reaction, the inventors focused on a reaction rate and discussed optimal conditions that allow the reaction speed to be as high as possible because the present invention synthesizes only a small quantity of $^{18}$F-labeled azide compound, making it indispensable to find such conditions that two very dilute substrates can be reacted under moderate conditions.

The inventors discussed the reaction conditions by using a non-labeled $^{19}$F azide compound as the substrate of the alkyne compound, a model of which is N-(prop-2-ynyl)benzamide. First, the high-concentrated substrates were subjected to the Huisgen reaction for screening of organic solvents most suitable for the reaction. 1 mM/L copper sulfate was used as a catalyst, 2 mM/L sodium ascorbate was used as a reducer, 1 mM/L TBTA was used in the Huisgen reaction. Further, the organic solvents were variously changed at the capacity ratio of water to organic solvent=3 to 7.

As a result, it was learnt that the addition of the non-protic solvent improved the yield, and the DMSO particularly improved the yield as illustrated in Table 2. Further, it was clearly known from the comparison of the entries 5 and 6 that the addition of TBTA dramatically improved the yield.

TABLE 2

| entry | solvent[a] | yield (%)[b] |
| --- | --- | --- |
| 1 | dioxane | 94 |
| 2 | DMF | 82 |
| 3 | CH3CN | 1 |
| 4 | t-BuOH | 95 |

TABLE 2-continued

| entry | solvent[a] | yield (%)[b] |
|---|---|---|
| 5 | DMSO | 97 |
| 6 | DMSO[c] | 8 |

[a]organic solvent:$H_2O$ = (7:3)
[b]yield obtained from HPLC
[c]TBTA not added

The inventors further looked into the reaction conditions in the foregoing reaction when a dilute solution is used. Similarly to concentrations conventionally used in radiation labeling tests, they changed the reaction conditions using a more dilute substrate (100 μmol/L N-(prop-2-ynyl)benzamide and 50 μmol/L non-labeled $^{19}$F azide compound (1b)). Then, it was learnt that the yield improved when the TBTA concentration was equal to or higher than 100 μM/L, and the yield was better when (TBTA concentration)/(Cu concentration) was ½ than 1. Thus, it was confirmed that the ratio less than 1 could favorably improve the yield. Further, the yield is better when the reaction temperature is set to 40° C. than room temperature.

TABLE 3

| entry | Na Asc | TBTA | Cu | temperature | yield (%)[a] |
|---|---|---|---|---|---|
| 1 | 1000 | 1000 | 1000 | room temperature | 71 |
| 2 | 1000 | 500 | 1000 | room temperature | 79 |
| 3 | 500 | 250 | 500 | room temperature | 81 |
| 4 | 200 | 100 | 200 | room temperature | 67 |
| 5 | 100 | 50 | 100 | room temperature | 41 |
| 6 | 1000 | 500 | 1000 | 40° C. | 94 |
| 7 | 500 | 250 | 500 | 40° C. | 87 |

[a]yield obtained from HPLC reaction time: 15 minutes
reaction solvent: DMSO/$H_2O$=20/80, 10 mmol/L, sodium phosphate buffer pH7

Figure 4:
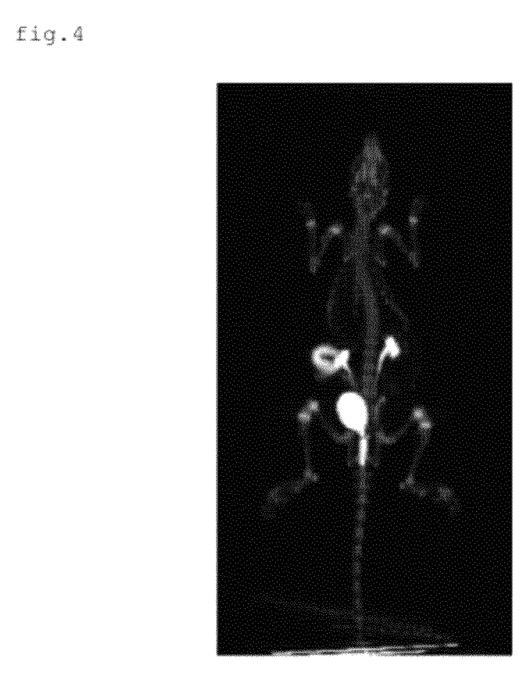
FIG. 4 is a whole-body image (MIP image) of a SD rat showing 30-minute accumulation after 120 minutes passed since an $^{18}$F-labeled oligonucleotide (5d) is administered to the SD rat though a caudal vein.

Under the conditions of the entry 2 in Table 3, the yield when pH of the sodium phosphate buffer is variously changed was checked. As illustrated in FIG. 4, the yield showed remarkable improvements when pH was 6.5 to 7.5, and marked the highest result when pH was around 7.

TABLE 4

| pH | yield (%) |
|---|---|
| 6.5 | 67 |
| 7 | 79 |
| 7.5 | 68 |

Under the conditions of the entry 2 in Table 3, the yield when the DMSO concentration is variously changed was checked. As illustrated in FIG. 5, the yield showed remarkable improvements when the DMSO volume percent is at least 30%.

TABLE 5

| DMSO (volume %) | yield (%) |
|---|---|
| 10 | 82 |
| 20 | 79 |
| 30 | 92 |
| 40 | 90 |
| 50 | 92 |

PET Images

Figure 1:
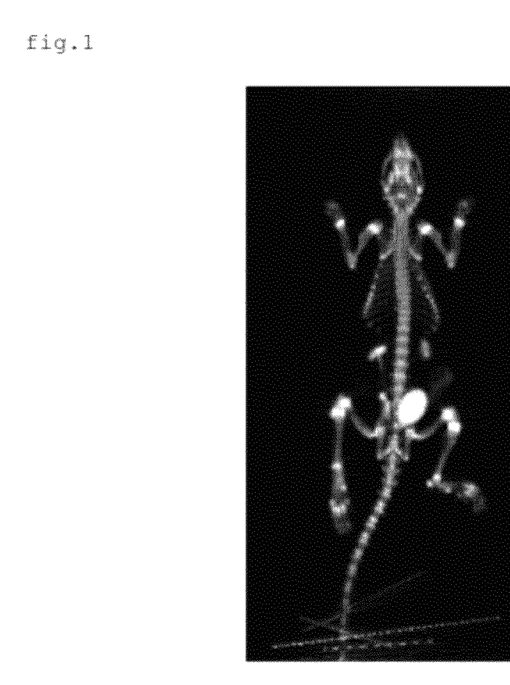
FIG. 1 is a whole-body image (MIP image) of an SD rat showing 30-minute accumulation after 120 minutes passed since an $^{18}$F-labeled oligonucleotide (5a) is administered to the SD rat though a caudal vein.

The $^{18}$F-labeled oligonucleotide (5a) obtained in the example 1 was administered to a rat, and a PET image was obtained. More specifically, a physiological salt solution containing 45 MBq of the $^{18}$F-labeled oligonucleotide (5a) is administered to an SD rat (8 weeks old, weight: 252 g) under anesthesia though a caudal vein, and an image of the rat was obtained by MicroPET Focus-220, PET apparatus for animals supplied by SIEMENS. FIG. 1 shows a whole-body image of the rat showing 30-minute accumulation after 120 minutes passed since the probe administration (Maximum Intensity Projection image). The image teaches that the administered $^{18}$F-labeled oligonucleotide (5a) was promptly metabolized in blood and excreted in urine. It is read from the image the deposition of intensive radiation in the bone texture of the whole body, which is, however, considered to result from F-ions generated as the $^{18}$F-labeled oligonucleotide (5a) is metabolized.

Figure 2:
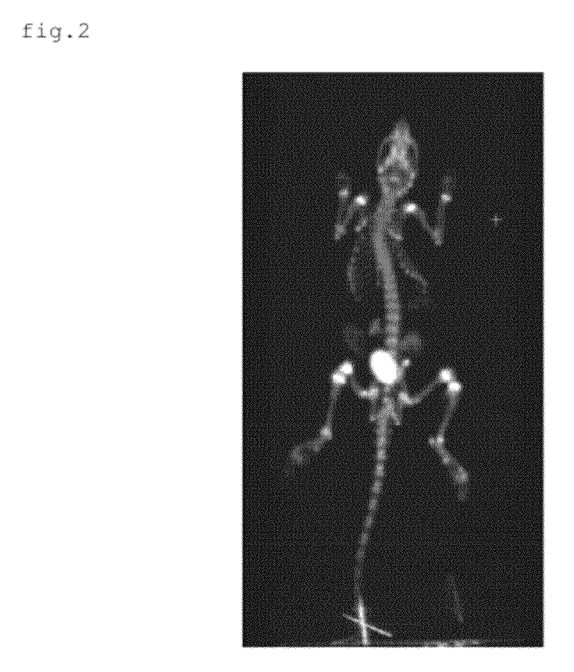
FIG. 2 is a whole-body image (MIP image) of a SD rat showing 30-minute accumulation after 120 minutes passed since an $^{18}$F-labeled oligonucleotide (5b) is administered to the SD rat though a caudal vein.
Figure 3:
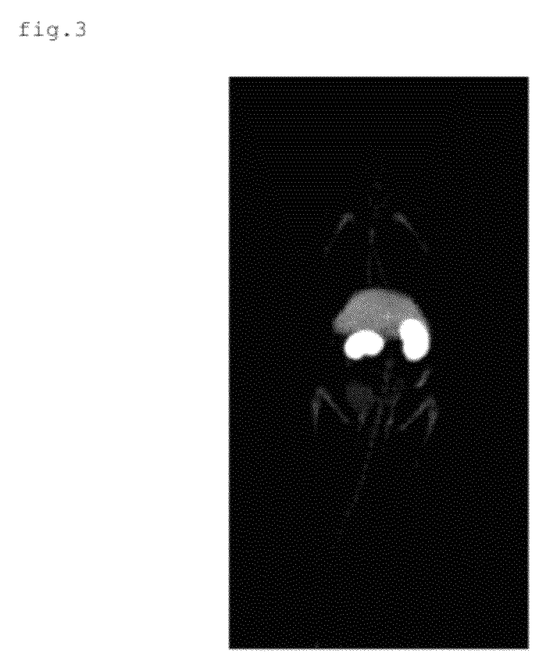
FIG. 3 is a whole-body image (MIP image) of a SD rat showing 30-minute accumulation after 120 minutes passed since an $^{18}$F-labeled oligonucleotide (5c) is administered to the SD rat though a caudal vein.

The $^{18}$F-labeled oligonucleotides (5b), (5c), and (5d) were similarly administered to rats, and PET images of the rats were obtained. FIGS. 2 to 4 show whole-body images of the rats showing 30-minute accumulation after 120 minutes passed since the administration (Maximum Intensity Projection image). These drawings teach that the 2',4'-BNA-transformed (5d), because its metabolic rate in blood slows down, is deposited in their kidneys and urinary bladders, and the radioactivity in their bone textures is deteriorated, and further teaches that the 2',4'-BNA-transformed (5c) having its skeleton bonded to phosphorothioate is metabolized at even a lower metabolic rate and deposited in the kidneys and urinary bladders, and the radioactivity in the bone textures is further deteriorated.

As described so far, when the $^{18}$F-labeled oligonucleotide according to the present invention is used, the effects of artificial nucleic acids, such as 2',4'-BNA-transformed oligonucleotide and phosphorothioate oligonucleotide, can be directly observed. Thus, the present invention is advantageous in that, for example, nuclease tolerance and distribution to tissues can be directly observed in vivo in the studies of the gene therapy using RNA interference. Therefore, the present invention can be leveraged as a technically advantageous tool in the research and development of oligonucleotide pharmaceutical products.

The present invention is not necessarily limited to the exemplary embodiment and examples described so far. The present invention includes various modified embodiments as far as they stay within the Scope of Claims and can be easily assumed by the ordinarily skilled in the art.

INDUSTRIAL APPLICABILITY

The present invention can provide an advantageous means in the field of medicine where nucleic acid oligomer is used, for example, RNA drug development expected to be launched in individualized medicine.

What is claimed is:

1. An $^{18}$F-labeled azide compound expressed by the following structural formula 1:

(1)

2. A reagent for $^{18}$F-labeling including the $^{18}$F-labeled azide compound according to claim 1.

3. A method for $^{18}$F-labeling of an alkyne compound, wherein Huisgen reaction is performed between the alkyne compound and the $^{18}$F-labeled azide compound according to claim 1 in the presence of a copper compound catalyst to obtain an $^{18}$F-labeled triasole derivative.

4. The method for $^{18}$F-labeling of the alkyne compound according to claim 3, wherein the reaction is performed in the presence of ascorbate and an amine-based base by using a mixed solvent including water and a water-soluble organic solvent as a reaction solvent.

5. The method for $^{18}$F-labeling of the alkyne compound according to claim 4, wherein the amine-based base is (tris ((1-benzyl-1H-1,2,3-triasole-4-yl)methyl)amine.

6. The method for $^{18}$F-labeling of the alkyne compound according to any one of claims 3 to 5, wherein the alkyne compound is a nucleotide derivative.

* * * * *